United States Patent [19]

Galin

[11] 4,305,905

[45] Dec. 15, 1981

[54] PROCESS FOR THE TERMINAL STERILIZATION OF INTRAOCULAR LENS

[76] Inventor: Miles A. Galin, 113 E. 39th St., New York, N.Y. 10016

[21] Appl. No.: 170,592

[22] Filed: Jul. 21, 1980

[51] Int. Cl.$^3$ .................... A01N 59/00; A61L 2/18
[52] U.S. Cl. .................................. 422/28; 53/526; 422/34; 424/127
[58] Field of Search ............... 422/28, 34; 424/127; 53/426

[56] References Cited

U.S. PATENT DOCUMENTS 4,013,576 3/1977 Loshaek ........................... 422/28 X
4,230,663 10/1980 Forstrom et al. ................. 422/28 X

OTHER PUBLICATIONS

Galin et al., "Sodium Hydroxide Sterilization of Intraocular Lenses", Amer. J. of Ophthalmology, vol. 88, No. 3, Part II, 9/79, pp. 560–564.

Galin et al., "Studies of Intraocular Lens Sterilization: The Effect of NaOH on *B. Subtilis* Spores", Amer. Intra-Ocular Implant Soc. J, vol. 6, 1/80; pp. 18–20.

*Primary Examiner*—Barry Richman
*Attorney, Agent, or Firm*—Brumbaugh, Graves, Donohue & Raymond

[57] ABSTRACT

Intraocular lenses are terminally sterilized without any significant chemical change in the surface of the lenses by placing the intraocular lenses in a 5% to 10% sodium hydroxide solution for from 24 hours to 3 hours, respectively, and storing the intraocular lenses in the same solution until they are used.

5 Claims, No Drawings

PROCESS FOR THE TERMINAL STERILIZATION OF INTRAOCULAR LENS

The present invention relates to a process for the terminal sterilization of intraocular lenses.

The Food and Drug Administration requires that a product be terminally sterilized. This means that the final form of the product and/or its container should be sterilized rather than sterilization be carried out in steps. For example, if a technician were to sterilize an intraocular lens and, physically using sterile forceps, transfer this sterile lens into a sterile bottle, all of these steps fit the term "sterile", yet the potential for error exists and this process would not be acceptable by the FDA. The FDA would, however, in this example, accept the placement of the product into the bottle and then the entire entity sterilized. This is terminal sterilization.

In 1952, an intraocular lens sterilization technique using 1% centrimide (a quaternary ammonium compound) was introduced. However, centrimide was suspected of being an occular irritant which causes severe inflammatory reactions including hypopyon. Ultraviolet irradiation was then used for implant sterilization. The wavelength of this irradiation, however, is strongly absorbed by polymethylmethacrylate and causes degradation of the acrylic as shown by a color change in the lens. The efficacy of this technique against certain spores has also been questioned.

For nearly thirty years, intraocular lenses of polymethylmethacrylate (PMMA) have been sterilized by the Ridley method wherein the lenses are placed in 10% NaOH solution at 30° C.-33° C. for 1 hour, transferred and stored in 0.1% NaOH solution and then rinsed with 0.5% $NaHCO_3$ before use. This technique is still employed in Europe but has been abandoned in the United States both because it is not a terminal form of sterilization and because the 0.1% NaOH concentration in which the lens is stored prior to use is an unsatisfactory sterilizing solution if seeded with a large innoculum, such as $10^6$ organisms/ml. In addition, the $NaHCO_3$ buffering solution used in the Ridley method has been a source of contamination in more than one case of intraocular infection.

Ethylene oxide (ETO) is the mandated terminal form of sterilization in the United States for intraocular lenses. There are questions of carcinogenicity for this agent and there is little known concerning its effects and the effects of minute concentrations of its breakdown products (ethylene chlorhydrin and ethylene glycol) on intraocular tissue. However, ETO has proved a safe and effective sterilizing agent according to the preliminary data from the FDA on the ongoing implant clinical investigation. The potential still exists, however, for sterilizing unclean lenses with ETO and introducing foreign, but sterile, material into the eye. In addition, in some quarters, a clinical expression exists that the incidence of sterile hypopyon is higher in ETO sterilized lenses. Consequently, a search persists for a sterilization method that combines the best attributes of the cleaning and sterilization potential of NaOH and the terminal sterilization benefits of ETO.

The present invention provides a process for the terminal sterilization of an intraocular lens without any significant chemical change in the lens surface which comprises placing the intraocular lens in a 5% to 10% sodium hydroxide (NaOH) solution (usually at a temperature of about 20° C.-33° C.) for from 24 hours to 3 hours, respectively, and storing the intraocular lens in the same solution (usually at room temperature, i.e., about 20° C.) until it is used. Preferably the terminal sterilization is achieved by placing the intraocular lens in a 10% NaOH solution for 3 hours at room temperature or in a 5% NaOH solution for 24 hours at room temperature and storing the intraocular lens in the same solution at room temperature prior to use. As the concentration of the terminal sterilization solution which is used increases from 5% to 10% NaOH, the sterilization time conversely decreases from 24 hours to 3 hours.

The terminal sterilization solution having the intraocular lens therein is suitably contained in an alkali-resistant polymethylpentene container. Under appropriate conditions of pressure and temperature, the outer surface of this container can be sterilized with ethylene oxide without the contents being subjected to this chemical.

Therefore, in order to sterilize the outside of the container and keep the outside sterile, the container with its contents is blister wrapped in polyethylene sheeting and sterilized with ethylene oxide gas. In the operating room the terminally sterilized intraocular lens is merely rinsed in sterile water prior to implantation in the eye.

The process of the present invention is particularly useful with looped or iris supported intraocular lenses which are more difficult to sterilize due to accompanying tunnels and irregular surfaces than are solid, biconvex intraocular lenses.

The process of the present invention is illustrated by the data presented below.

Materials, Methods and Results

A. Test Organisms:
*Bacillus subtilis* var. niger: ATCC #9372
*Paecilomyces lilacinus:* ATCC #13357
*Aspergillus fischeri:* ATCC #1020

B. Preparation of Inocula:

1. *Bacillus subtilis:* Cultured for 5 days at 25° C. on Trypitic Soy Agar containing 0.3 ml/l $MnSO_4$. Harvest was suspended in distilled water, washed three times by centrifugation and resuspended in distilled water. The suspension was heat shocked for 3 minutes at 80° C. Spore count was determined by plating. Suspension was diluted to $10^6$ organisms/ml in 80% isopropanol (w/v) and confirmed by plate count.

2. *Paecilomyces lilacinus:* Cultured for 7 days at 25° C. on Sabouraud Maltose Agar. Harvest was suspended in phosphate buffer, washed three times by centrifugation and resuspended in phosphate buffer. Spore count was determined by plating. Suspension was diluted to $10^6$ organisms/ml and confirmed by plate count.

3. *Aspergillus fischeri:* Cultured for 11 days at 25° C. on Malt Agar. Harvest was suspended in phosphate buffer and lightly homogenized in tissue grinder to give heavy ascus/ascospore suspension. Filtered through pyrex wool. Spore count was determined by plating. Suspension was diluted to $10^6$ organisms/ml and confirmed by plate count.

C. Phosphate buffer (Buffered Ringer's Solution):

| Ingredient | g/l |
| --- | --- |
| NaCl | 8.6 |
| $CaCl_2$ | 0.33 |
| KCl | 0.30 |
| $Na_2H\ PO_4$ | 42.58 |

| Ingredient | g/l |
|---|---|
| KH$_2$PO$_4$ | 27.22 |
| Distilled Water | Q.S. 1 liter |

D. Procedure:

1. Three tubes were prepared; each separately contained 4.0 ml with approximately 10$^6$ organisms/ml of one of the above three organisms.
2. A looped PMMA intraocular lens was placed in each tube in a 30° C. water bath.
3. 1 ml 25% NaOH was added to each tube to obtain 5% NaOH final concentration.
4. 24 hour contact at 30° C. was allowed.
5. The contents were well mixed and 4 separate 1 ml portions were withdrawn from each tube and transferred to 4 separate 9 ml tubes of phosphate buffer containing sufficient HCl to neutralize 1 ml of the NaOH used.
6. 2 ml portions of neutralized solution were removed from each of 2 tubes, plated on Tryptic Soy Agar (TSA) and incubated at room temperature for 7 days.
7. The entire neutralized contents of each of the remaining 2 tubes were filtered through a separate 0.45 μm membrane filter. Each filter was transferred to 100 ml Tryptic Soy Broth (TSB) and incubated at room temperature for 7 days.

RESULTS

I. *Bacillus Subtilis* (spores)—24 hrs. at 30° C. in 5% NaOH—lens mixture.

TABLE 1

| Pour Plate Recovery (TSA) - No. Colonies after 7 days Room Temperature | | |
|---|---|---|
| Tube No. | TSA Plate A | TSA Plate B |
| 1 | 0 | 0 |
| 2 | 0 | 0 |

4/4 plates negative

TABLE 2

| Membrane Filtration Sterility Test (TSB) - Growth after 7 days Room Temperature | |
|---|---|
| Tube No. | Growth |
| 3 | 0 |
| 4 | 0 |

2/2 filters sterile

TABLE 3

| Pour Plate Recovery (TSA) - No. Colonies after 7 days Room Temperature | | |
|---|---|---|
| Tube No. | TSA Plate A | TSA Plate B |
| 1 | 0 | 0 |
| 2 | 0 | 0 |

4/4 plates negative

TABLE 4

| Membrane Filtration Sterility Test (TSB) - Growth after 7 days Room Temperature | |
|---|---|
| Tube No. | Growth |
| 3 | 0 |
| 4 | 0 |

2/2 filters sterile

TABLE 5

| Pour Plate Recovery (TSA) - No. Colonies after 7 days Room Temperature | | |
|---|---|---|
| Tube No. | TSA Plate A | TSA Plate B |
| 1 | 0 | 0 |
| 2 | 0 | 0 |

4/4 plates negative

TABLE 6

| Membrane Filtration Sterility Test (TSB) - Growth after 7 days Room Temperature | |
|---|---|
| Tube No. | Growth |
| 3 | 0 |
| 4 | 0 |

2/2 filters sterile

SUMMARY

A 5% solution of NaOH in three simulated contaminated lens solutions rendered high concentrations (10$^6$ organisms/ml) of spores of *Aspergillus fischeri*, *Paecilomyces lilacinus* and *Bacillus subtilis* nonviable after 24 hours at 30° C., as judged by failure to recover the respective organisms by either pour plate or membrane filtration techniques.

In further experimental tests, looped PMMA intraocular lens were contaminated with 10$^6$ organisms/ml of *Bacillus subtilis* spores or with 10$^6$ organisms/ml of three organism pools (Pool No. 1 contained *Bacillus subtilis*, Cornyebacterium sp., *Enterobacter agglomerans*, *Pseudomonas aeruginosa*, *Pseudomonas cepacia*, *Staphlococcus aureus* and *Aspergillus niger*; Pool No. 2 contained *Escherichia coli*, *Staphylococcus aureus*, *Pseudomonas aeruginosa* and *B-Hemolytic streptococcus*; Pool No. 3 contained *Proteus* sp., *Pseudomonas maltophilia*, *Aspergillus niger* and *Bacillus subtilis*) and then placed in 10% NaOH at 33° C. for 1 hour (Pool No. 1) or 3 hours (Pool Nos. 2 and 3). It was found that the use of 10% NaOH at 33° C. for 1 hour (Ridley method) was ineffective for terminal sterilization (positive cultures were obtained), whereas the use of 10% NaOH at 33° C. for 3 hours was effective for terminal sterilization (no positive cultures were obtained). These findings are reported in my two co-authored articles entitled "Sodium Hydroxide Sterilization of Intraocular Lenses" and "Studies of Intraocular Lens Sterilization: The Effect of NaOH on *B. subtilus* Spores" appearing, respectively, in American Journal of Ophthalmology, Vol. 88, No. 3, Part II, pages 560–564, September, 1979, and in American Intra-Ocular Implant Society Journal, Vol. 6, pages 18–20, January, 1980, the entire contents of which two articles co-authored by me are hereby incorporated by reference herein.

In comparative experimental tests, it was found that 1%, 2% and 3% NaOH solutions were not effective sterilizers of intraocular lens contaminated with 10$^6$ organisms/ml of *Bacillus subtilis* var. niger when using a contact time of up to 5 hours.

A strong base, such as 10% NaOH, could hydrolyze the surface methyl ester groups according to the following reaction:

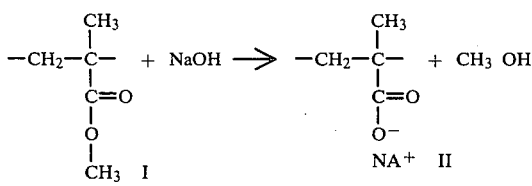

where I represents one subunit of the PMMA molecule at the lens surface. If this surface hydrolysis occurs, the lens surface would change from neutral to anionic (negative). Also, since sodium polymethacrylate, the homopolymer of complete structure II, is highly water-soluble, whereas PMMA is water-insoluble, the surface would be expected to become more hydrophilic as surface hydrolysis occurred. Because of these possibilities, a study was undertaken to ascertain the effect of strong base (10% NaOH) on the surface of a PMMA intraocular lens in order to determine whether the lens could be sterilized and stored (terminal sterilization) without significant chemical change in the lens surface.

Materials, Methods and Results

PMMA (Perspex CQ) was obtained from the same sheets used to make iris clip and anterior chamber lenses and was provided as a clear sheet of material sandwiched between two sheets of "waxed" paper. Sixteen 1 cm$^2$ samples were used for contact angle measurements, and eight 2 cm$^2$ samples were used for electron spectroscopy chemical analysis (ESCA) studies. No pieces with gross defects, such as scratches, chips or cracks caused by cutting, were chosen as test specimens. Each sample was cleaned with a mild detergent and then exhaustively rinsed in a deionized water.

Contact angles were measured at 20° C. on each sample using a drop image projection technique whereby the shadow of a drop is projected onto a screen calibrated for angle measurements to the nearest 1°. Contact angles were 60°±2° in all cases. Eight 1 cm$^2$ pieces were then submerged in 10% NaOH at 20° C. for periods from 5 minutes to 4 days. The samples were removed, rinsed and their contact angles measured. No change from the original contact angle was observed. The other eight 1 cm$^2$ samples were placed in 10% NaOH at 50° C. for up to 1160 hours (approximately equivalent to 9,000 hours at room temperature). Contact angles (60°±2° after 12 hours and 59°±2° after 1160 hours) were essentially unchanged.

ESCA analysis, which is capable of detecting specific atoms in concentrations as low as 1% (atomic), was performed on the eight 2 cm$^2$ samples. The specimens were submerged in a 10% KOH solution at 50° C. for up to four days. Controls were treated with deionized water only. Potassium hydroxide was used instead of NaOH, because of possible contamination by environmental sodium. Broadband spectra and shortscans of the carbon 1s/potassium 2p binding energy region in ESCA were taken for each sample. From these measurements, it is possible to determine the elemental composition of the surface (20–50 Å deep), including the percentage of carbon atoms that are carbonyl carbon (C═O) or hydrocarbon carbon

as well as the percent of surface K$^+$. Elemental composition of control and experimental samples were identical (±1 atom/100 atoms), and no potassium was detected.

There was, therefore, no evidence of hydrolysis or chemical change in the lens surface even upon extended storage in the strongest base concentration (10%) used in the process of the present invention.

It has been found that intraocular lenses which were terminally sterilized by the process of the present invention maintained their sterility for at least 2 years of shelf life.

What is claimed is:

1. A process for the terminal sterilization of an intraocular lens without significant chemical change in the lens surface which comprises placing the intraocular lens in a 5% to 10% sodium hydroxide solution for from 24 hours to 3 hours, respectively, and storing the intraocular lens in the same solution until it is used.

2. The process as defined by claim 1 wherein the intraocular lens is placed in a 5% sodium hydroxide solution at about 20° C.–33° C. for 24 hours and the intraocular lens is stored in the same solution at about 20° C. until it is used.

3. The process as defined by claim 1 wherein the intraocular lens is placed in a 10% sodium hydroxide solution at about 20° C.–33° C. for 3 hours and the intraocular lens is stored in the same solution at about 20° C. until it is used.

4. The process as defined by claim 1 wherein said intraocular lens is a polymethylmethacrylate looped intraocular lens.

5. The process as defined by claim 1 wherein said solution with the intraocular lens therein is contained in an alkali-resistant polymethylpentene container, and further including the step of subsequently blister wrapping the container in polyethylene sheeting and exposing the exterior of the package to gaseous ethylene oxide to thereby sterilize the exterior of the container.

* * * * *

UNITED STATES PATENT AND TRADEMARK OFFICE
CERTIFICATE OF CORRECTION

PATENT NO. : 4,305,905
DATED : Dec. 15, 1981
INVENTOR(S) : Miles A. Galin

It is certified that error appears in the above—identified patent and that said Letters Patent is hereby corrected as shown below:

Col. 1, line 57, "expression" should read --impression--.

Col. 3, following line 50 and before "TABLE 3", insert the following paragraph: --II. Paecilomyces Lilacinus (spores) - 24 hrs. at 30°C. in 5% NaOH - lens mixture.--.

Col. 4, before "TABLE 5" (line 1), insert the following paragraph: --III. Aspergillus Fischeri (spores) - 24 hrs. at 30°C. in 5% NaOH - lens mixture.--.

Signed and Sealed this

Thirteenth Day of April 1982

|SEAL|

Attest:

GERALD J. MOSSINGHOFF

*Attesting Officer*     *Commissioner of Patents and Trademarks*